US006716997B1

(12) United States Patent
Zoeller (10) Patent No.: US 6,716,997 B1
(45) Date of Patent: Apr. 6, 2004

(54) SYSTEMS AND METHODS FOR GENERATION OF ASCORBIC ACID WITH REDUCED COLOR

(75) Inventor: Joseph R. Zoeller, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/267,404

(22) Filed: Oct. 9, 2002

Related U.S. Application Data
(60) Provisional application No. 60/327,884, filed on Oct. 9, 2001.

(51) Int. Cl.$^7$ ............................................. C07D 307/62
(52) U.S. Cl. ....................................................... 549/315
(58) Field of Search .......................................... 549/315

(56) References Cited

U.S. PATENT DOCUMENTS

| | | | |
|---|---|---|---|
| 2,185,618 | A | 1/1940 | Welch et al. |
| 2,265,121 | A | 12/1941 | Reichstein |
| 2,462,251 | A | 2/1949 | Bassford, Jr. et al. |
| 2,491,065 | A | 12/1949 | Eekelen et al. |
| 3,007,941 | A | 11/1961 | Copelin et al. |
| 3,257,417 | A | 6/1966 | Dunlop et al. |
| 4,767,870 | A | 8/1988 | Fujiwara et al. |
| 4,778,902 | A | 10/1988 | Fujiwara et al. |
| 5,128,487 | A | 7/1992 | Tomislav et al. |
| 5,391,770 | A | 2/1995 | Le Fur et al. |
| 5,744,618 | A | 4/1998 | Frechtel et al. |
| 5,817,238 | A | 10/1998 | Makino et al. |
| 6,004,445 | A | 12/1999 | Genders et al. |
| 6,197,977 | B1 | 3/2001 | Bottcher et al. |
| 6,235,673 | B1 | 5/2001 | Zoeller et al. |

FOREIGN PATENT DOCUMENTS

| | | |
|---|---|---|
| CH | 428815 | 5/1935 |
| DE | 38 19 045 A | 12/1988 |
| DE | 38 43 389 | 6/1990 |
| DE | 197 34086 | 8/1998 |
| EP | 0 403 351 A | 12/1990 |
| EP | 0 554 090 | 4/1993 |
| GB | 1222322 | 2/1971 |
| GB | 2034315 | 6/1980 |
| JP | 73015931 | 5/1973 |
| JP | 55-94394 A | 7/1980 |
| JP | 55094394 | 7/1980 |
| WO | WO 87/00839 | 2/1987 |
| WO | WO 97/13761 | 4/1997 |
| WO | WO 99/07691 | 8/1998 |
| WO | WO 00/46216 | 7/2000 |

OTHER PUBLICATIONS

International Search Report, mailing date Dec. 20, 2002, for PCT/US02/32259, international filing date Sep. 10, 2002.
Anderson, S. et al., Production of 2–Keto–L–Gulonate, an Intermediate in L–Ascorbate Synthesis, by a Genetically Modified *Erwinia herbicola*, *Science*, 230, 144–149 (1985).

Eschinazi, H. E., La décarbonylation des aldéhydes et la déhydes et la déshydracarbonylation des alcohols par voie catalytique au palladium, *Bull. Soc. Chim. Fr.*, 967–969 (1952).

Japan Kokai, 1531; 1532; 1533, Furans, *Chemical Abstracts*, 64, 12644 (1966).

Jung, K. J. et al., Furan by Decarbonylation of Furfural, *Informations Chemie*, 283, 135–138 (1987) English translation.

Jung, K. J. et al., Furfural Decarbonylation Catalyzed by charcoal Supported Palladium: Part I—Kinetics, *Biomass*, 16, 63–76 (1988).

Jung, K. J. et al., Furfural Decarbonylation Catalyzed by Charcoal Supported Palladium: Part II, *Biomass*, 16, 89–97 (1998).

Kuz'Micheva, E. L., Development of Catalyst for Furan Manufacture, *Uzbeskskii Khimicheski Zhurnal*, 46–48 (1999) English translation.

Lejemble, Ph., et al., An Improved Method to Prepare Catalysts for the Selective Decarbonylation of Furan–2 Carboxaldehyde into Furan, *Chem. Lett.*, 1403–06 (1983).

Lejemble, Ph., et al., From Biomass to Furan through Decarbonylation of Furfural under Mild Conditions, *Biomass*, 4, 263–274 (1984).

Regna, P. P. et al., Kinetics of Transformation of 2–Ketopolyhydroxy Acids, *J. Am. Chem. Soc.*, 66, 246–250 (1994).

Reichstein, T. et al., Eine Ergiebige Synthese der 1–Ascorbinsäure (C–Vitamine)$^2$), *Chim. Acta*, 17, 311–32 (1934).

Saito, Y., Direct Fermentation of 2–Keto–L–Gulonic Acid in Recombinant Gluconobacter Oxydans, *Biotechnol. Bioeng.*, 58, 309–315 (1998).

Singh, H. et al., Metal Support Interaction in the Palladium—catalysed Decomoposition of Furfural to Furan, *J. Chem. Tech. Biotechnol.*, 30, 293–296 (1980).

*Primary Examiner*—Amelia A. Owens
(74) *Attorney, Agent, or Firm*—Kilpatrick Stockton LLP; Charles Calkins; Cynthia B. Rothschild (57) ABSTRACT

The present invention describes the synthesis of ascorbic acid with reduced color. The present invention employs palladium catalysts for the synthesis of ascorbic acid from 2-keto-gulonic acid or derivatives of 2-keto-gulonic acid. The palladium catalyst may include an inert support such as, but not limited to, carbon or barium sulfate. Unlike other palladium catalysts, the catalyst of the present invention is active under aqueous conditions suitable for ascorbic acid synthesis. Also described are systems for the conversion of 2-keto-gulonic acid or derivatives of 2-keto-gulonic acid to ascorbic acid in the presence of a solid palladium catalyst and ascorbic acid of reduced color made by the methods of the present invention.

73 Claims, 2 Drawing Sheets

SYSTEMS AND METHODS FOR GENERATION OF ASCORBIC ACID WITH REDUCED COLOR

CROSS REFERENCE TO RELATED APPLICATIONS

This application claims priority to U.S. Provisional Application Serial No. 60/327,884, filed Oct. 9, 2001. The disclosure of U.S. Provisional Application Serial No. 60/327,884 is incorporated herein by reference.

FIELD OF THE INVENTION

The present invention relates to methods and systems for producing L-ascorbic acid with reduced color. Specifically, the present invention relates to ascorbic acid with reduced color formed using palladium supported catalysts.

BACKGROUND OF THE INVENTION

L-Ascorbic acid (vitamin C) is produced commercially by combined chemical and fermentation processes starting from glucose or sorbose. A common intermediate generated in the commercial process is 2-keto-L-gulonic acid (KLG), or its protected form, diacetone-2-keto-L-gulonic acid. The conversion of 2-keto-L-gulonic acid to L-ascorbic acid may be carried out by esterification with methanol, followed by cyclization using stoichiometric amounts of a base, in a methodology derived from the original Reichstein process (T. Reichstein, A. Grussner, Helv. Chim. Acta 17, pp. 311–328, 1934). Alternatively, diacetone-2-keto-L-gulonic acid may be cyclized directly, with a loss of acetone followed by consecutive lactonization and enolization, to form ascorbic acid. Direct cyclization of diacetone-2-keto-L-gulonic acid requires extensive purification for recovery of the acetone and other by-products generated.

Modifications to the Reichstein process have focused on removal or simplification of many of the chemical processing steps required for the production of 2-keto-L-gulonic acid. Improvements include controlled esterification of 2-keto-L-gulonic acid and subsequent removal of unesterified starting material (U.S. Pat. No. 5,128,487), as well as improved integration of esterification with subsequent cyclization (U.S. Pat. No. 5,391,770).

Efforts have also been directed to acid catalysis (e.g. U.S. Pat. No. 2,462,251; GB 1,222,322; GB 2,034,315; DE 19734086, DE 3843389; WO 99/07691; and WO 00/46216) thereby removing the steps of esterification with subsequent based-catalyzed cyclization and reprotonation of the L-ascorbic acid product. In addition, modifications to improve the process such as the use of organic solvents and surfactants have been described (see e.g. U.S. Pat. No. 5,744,618; WO 87/00839; and JP-B 73015931).

An alternative means of producing ascorbic acid from 2-keto-L-gulonic acid involves an aqueous intramolecular cyclization process without the use of copious amounts of acid catalysts (T. Reichstein, Helv. Chim. Acta 17, 1934, pp.311–328 and BP 428,815). Although aqueous cyclization does not require the extensive purification steps associated with acid catalysis, non-acid catalyzed intramolecular cyclization is associated with relatively low yields. For example, 2-keto-L-gulonic acid may be heated in water saturated with carbon dioxide with a 50% yield after fractional crystallization (U.S. Pat. No. 2,265,121). Also, 2-keto-L-gulonic acid or derivatives of 2-keto-L-gulonic acid may be heated to 130–140° C. in water to generate ascorbic acid with yields approximating 50% (U.S. Pat. No. 2,491,065).

A common problem encountered with conversion of 2-keto-L-gulonic acid to ascorbic acid in water or acidic solutions is the production of colored solutions from degradation products that are formed during the reaction. These degradation products generally include high molecular weight compounds that accumulate as a function of conversion. Thus, with increasing conversion, solutions tend to become increasingly colored and eventually form insoluble by-products. Generally, methods to decolor ascorbic acid involve adsorption of the colored by-products using carbon or other solid supported agents. The use of large amounts of carbon or other solid decolorizing agents significantly hinders subsequent purification of the L-ascorbic acid product and ultimately, may become cost prohibitive.

Thus, there is a need for improved methods and agents to reduce the formation of color when ascorbic acid is produced by aqueous or acid catalysis. There is also a need for a heterogeneous catalyst that can be easily separated from the ascorbic acid product. Ideally, the agents used for reducing the formation of color employ materials that are relatively inexpensive, non-toxic, and easy to handle. Also ideally, the agent used contributes to catalysis of the reaction. Even more ideally, such color reducing catalysts are useable in systems that allow for separation of the catalyst from the reaction components. Also ideally, such color reducing should allow for recycling of unused starting compounds and/or catalyst when the synthesis is taken only to partial conversion, as for example, to avoid excessive degradation of ascorbic acid product.

SUMMARY OF THE INVENTION

The present invention describes the synthesis of ascorbic acid with reduced color using palladium (Pd) as a heterogeneous catalyst. The palladium catalyst may include an inert support such as, but not limited to, carbon or barium sulfate. Unlike other palladium catalysts, the catalyst of the present invention is active under aqueous conditions suitable for ascorbic acid synthesis.

Thus in one aspect, the present invention comprises a method for reducing the amount of color formed when ascorbic acid is synthesized from 2-keto-gulonic acid or 2-keto-gulonic acid derivatives comprising conducting the synthesis in the presence of palladium. In an embodiment, the palladium at least in part reduces the formation of colored byproducts in the reaction.

In another aspect, the present invention comprises ascorbic acid synthesized from 2-keto-gulonic acid or a 2-keto-gulonic acid derivative in the presence of palladium.

In yet another aspect, the present invention comprises a system for reducing the amount of color formed when ascorbic acid is synthesized from starting material comprising 2-keto-gulonic acid or a 2-keto-gulonic acid derivative comprising a reactor for conducting the synthesis in the presence of palladium.

The foregoing focuses on the more important features of the invention in order that the detailed description which follows may be better understood and in order that the present contribution to the art may be better appreciated. There are, of course, additional features of the invention which will be described hereinafter and which will form the subject matter of the claims appended hereto. It is to be understood that the invention is not limited in its application to the specific details as set forth in the following description and figures. The invention is capable of other embodiments and of being practiced or carried out in various ways.

From the foregoing summary, it is apparent that an object of the present invention is to provide methods and systems for synthesizing ascorbic acid from 2-keto-gulonic acid or a 2-keto-gulonic acid derivative to produce ascorbic acid that has relatively low levels of discoloration. More specifically, the present invention provides for the use of palladium as both a heterogeneous catalyst and as an agent to reduce the formation of color.

The present invention has several advantages over the prior art. For example, the palladium catalysts of the present invention provide for efficient synthesis of ascorbic acid in aqueous or acid conditions. The present invention may be used to prevent the formation of colored, high molecular weight byproducts and thus, improve the efficiency of the reaction and reduce purification costs. Also, as heterogeneous catalysts, the palladium catalysts of the present invention are easily removed from the ascorbic acid product. In addition, the palladium catalysis of the present invention may be used in established reactor formats such as stirred tank reactors, fluidized beds, or fixed bed reactors. These, together with other objects and advantages of the present invention along with various features of novelty which characterize the invention, are pointed out with particularity in the description, appended claims and accompanying drawings provided herein.

DETAILED DESCRIPTION

The present invention relates to methods and systems for the synthesis of ascorbic acid with reduced color formation. The method employs palladium catalysts for aqueous or acidic synthesis of ascorbic acid from 2-keto-gulonic acid or derivatives of 2-keto-gulonic acid. Although not wishing to be bound by theory, it is believed the catalysts of the present invention work by decarbonylation of furfural intermediates that generate highly colored, high molecular weight compounds. The use of palladium based catalysts reduces the amount of carbon and other decolorizing agents required for decolorization of the ascorbic acid product and thus, significantly simplifies purification of ascorbic acid from the reaction. The present invention also describes systems for the synthesis of ascorbic acid having reduced color. The systems of the present invention use inexpensive components and reagent systems and thus, can be scaled up for plant capacity as described herein.

Palladium Catalysts For Generation of Ascorbic Acid With Reduced Color

Thus, in one aspect, the present invention comprises a method for reducing the amount of color in ascorbic acid synthesized from 2-keto-gulonic acid or 2-keto-gulonic acid derivatives comprising conducting the synthesis in the presence of palladium.

In an embodiment, the palladium at least in part reduces the formation of colored byproducts. Also in an embodiment, the palladium at least in part catalyses the synthesis of ascorbic acid from 2-keto-gulonic acid or 2-keto-gulonic acid derivatives. Thus, the palladium may improve the overall efficiency of the synthesis of ascorbic acid from 2-keto-gulonic acid or 2-keto-gulonic acid derivatives.

Preferably, the ascorbic acid comprises L-ascorbic acid synthesized from 2-keto-L-gulonic acid or a 2-keto-L-gulonic acid derivative. In an embodiment, the 2-keto-L-gulonic acid comprises an aqueous solution from a fermentation process for producing 2-keto-L-gulonic acid. In another embodiment, the 2-keto-L-gulonic acid comprises an aqueous solution of 2-keto-L-gulonic acid derived from the hydrolysis of the bisacetonide of 2-keto-L-gulonic acid or the esters of 2-keto-L-gulonic acid. In an embodiment, the 2-keto-gulonic acid derivative comprises a 2-keto-gulonic acid ester.

Preferably, the synthesis of ascorbic acid is carried out in a solvent. More preferably, the solvent is moderately polar. In an embodiment, the solvent comprises water. Alternatively, the solvent may comprise an alcohol. Preferably, the alcohol comprises the alkoxy moiety of a 2-keto-L-gulonic acid ester used as the 2-keto-gulonic acid derivative.

Preferably, the palladium is supported on a particulate substrate. More preferably, the substrate comprises carbon or barium sulfate.

Also preferably, the catalyst comprises particles ranging in size from 1 $\mu$m to 5 cm. More preferably, the catalyst comprises particles ranging in size from 25 $\mu$m to 5 cm. More preferably, the catalyst comprises particles ranging in size from 100 $\mu$m to 2.5 cm. Even more preferably, the catalyst comprises particles ranging in size from 150 $\mu$m to 1.5 cm.

The amount of palladium which can be used is at least in part dependent on the size of the particles, with smaller particles allowing for a higher concentration of palladium in the reaction. Thus, the palladium on the support may range from 0.1 to 10 weight percent palladium or in alternate embodiments, from 0.1 to 5 weight percent palladium or from 1 to 3 weight percent palladium.

In an embodiment, the synthesis comprises heating the 2-keto-gulonic acid or 2-keto-gulonic acid derivative. The step of heating may be done at a temperature of from about 25 to about 250° C. More preferably, the step of heating is at a temperature of from about 75 to about 200° C. Also, the step of heating is generally performed under an absolute pressure of from about 0.1 to about 100 atm (1.5–1460 psi) and more preferably, under an absolute pressure of from about 0.7 to about 17 atm (10–250 psi).

Preferably, the synthesis of ascorbic acid from 2-keto-gulonic acid comprises an aqueous solution of 1 to 40 weight percent 2-keto-L-gulonic acid compound. More preferably, the synthesis comprises an aqueous solution of 5 to 30 weight percent 2-keto-L-gulonic acid compound. Even more preferably, the synthesis comprises an aqueous solution of 8 to 25 weight percent 2-keto-L-gulonic acid compound.

Also preferably, the conversion of 2-keto-L-gulonic acid substrate to L-ascorbic acid product preferably ranges from about 10% to 90%. More preferably, the conversion of 2-keto-L-gulonic acid substrate to L-ascorbic acid product ranges from about 20% to 80%. Even more preferably, the conversion of 2-keto-L-gulonic acid substrate to ascorbic acid product ranges from about 40% to 70%.

In an embodiment, the conversion of 2-keto-gulonic acid to ascorbic acid is taken to only partial conversion to avoid excessive degradation of ascorbic acid product. Thus, the method may also comprise the steps of: removing from the reactor a post-reaction solution comprising the unreacted 2-keto-gulonic acid compound and ascorbic acid; separating the ascorbic acid from unreacted 2-keto-gulonic acid compound in the post-reaction solution to form an ascorbic acid rich solution and a solution rich in the unreacted 2-keto-gulonic acid compound; and recycling the solution comprising unreacted 2-keto-gulonic acid compound to the reactor.

As used herein, the phrase "ascorbic acid rich solution" refers to an aqueous solution of ascorbic acid in which the ratio of ascorbic acid to 2-keto-gulonic acid has been increased relative to the post-reaction solution. Likewise, the phrase "2-keto-gulonic acid rich solution" or "solution rich in 2-keto-gulonic acid compound" refers to an aqueous solution of 2-keto-gulonic acid or derivatives thereof in which the ratio of 2-keto-gulonic acid compound to ascorbic acid product has been increased relative to the post-reaction solution. As used herein, derivatives of 2-keto-gulonic acid may comprise esters of 2-keto-gulonic acid, diacetone-2-keto-gulonic acid, and other derivatives of 2-keto-gulonic acid which may be cyclized to ascorbic acid. Generally, the L isomer is preferred.

In an embodiment, the palladium catalyst for reducing color is mixed with a second catalyst for increasing the conversion of starting 2-keto-gulonic acid or 2-keto-gulonic acid derivatives to ascorbic acid.

In a preferred embodiment, the reactor is a plug flow reactor. Preferably, the range of space velocities in the plug flow reactor is between 0.05 h$^{-1}$ to 500 h$^{-1}$. More preferably, the range of space velocities is between 0.1 h$^{-1}$ and 100 h$^{-1}$. Other reactor designs, such as continuous stirred tank reactor, wherein the catalyst is maintained as a slurry, or a trickle bed reactor may also be used.

In another aspect, the present invention comprises ascorbic acid synthesized from 2-keto-gulonic acid or a 2-keto-gulonic acid derivative in the presence of palladium. Preferably, the ascorbic acid comprises reduced color compared to ascorbic acid synthesized from 2-keto-gulonic acid or a 2-keto-gulonic acid derivative in the absence of palladium.

In an embodiment, the palladium at least in part reduces the formation of colored byproducts in the reaction. Also in an embodiment, the palladium at least in part catalyses the synthesis of ascorbic acid from 2-keto-gulonic acid or 2-keto-gulonic acid derivatives.

Preferably, the ascorbic acid is L-ascorbic acid synthesized from 2-keto-L-gulonic acid or a 2-keto-L-gulonic acid derivative. Thus, in an embodiment, the 2-keto-gulonic acid comprises an aqueous stream from a fermentation process for producing 2-keto-L-gulonic acid. Also in an embodiment, the 2-keto-gulonic acid derivative comprises a 2-keto-L-gulonic acid ester. In yet another embodiment, the 2-keto-gulonic acid comprises the hydrolysis of the bisacetonide of 2-keto-L-gulonic acid.

Preferably, the synthesis of ascorbic acid is carried out in a solvent. More preferably, the solvent is moderately polar. In an embodiment, the solvent comprises water. Alternatively, the solvent may comprise an alcohol. Preferably, the alcohol comprises the alkoxy moiety of a 2-keto-L-gulonic acid ester used as the 2-keto-gulonic acid derivative.

In an embodiment, the palladium is supported on a particulate substrate. Preferably, the substrate comprises barium sulfate or carbon. Preferably, the palladium comprises particles ranging in size from 1 µm to 5 cm, more preferably from 25 µm to 5 cm, more preferably, from 100 µm to 2.5 cm, and even more preferably, from 150 µm to 1.5 cm Preferably, the conversion of 2-keto-gulonic acid compounds to ascorbic acid is taken to only partial conversion to avoid excessive degradation of the ascorbic acid product. Even more preferably, the ascorbic acid product is separated from unreacted 2-keto-gulonic acid or a derivative thereof.

In an embodiment, the synthesis is carried out in a plug flow reactor although other types of reactors such as stirred tank reactors, fluidized beds and trickle bed fixed bed reactors may be used.

Thus, the present invention provides methods for making ascorbic acid having reduced color. A common problem encountered with conversion of 2-keto-L-gulonic acid to L-ascorbic acid in water or in the presence of acidic solutions is the production of colored solutions formed from degradation products. These degradation products generally comprise high molecular weight compounds that accumulate as a function of conversion. Thus, with increasing conversion, solutions tend to become increasingly colored and eventually form insoluble by-products.

Generally, methods to decolor ascorbic acid involve adsorption of the colored by-products using carbon or other solid supported agents. Ultimately, however, the use of large amounts of carbon or other solid decolorizing agents can significantly increase cost. For example, in addition to necessitating the purchase and disposal of large amounts of the adsorbent, the use of agents to remove color from the ascorbic acid product increases the need for substantial additions to the reactor to purify the absorbent from the L-ascorbic acid. In contrast, the present invention teaches the use of palladium catalysts to prevent color from being formed and thus, employs reagents and additional reactor units on a much smaller scale.

Without being bound to any theory, color bodies formed in aqueous or acid catalyzed synthesis of ascorbic acid from 2-keto-L-gulonic acid may result as a consequence of the decomposition of 2-keto-L-gulonic acid and ascorbic acid to furfural (2-furaldehyde) and subsequent polymerization. Whereas the decarbonylation of furfural (forming furan and either carbon monoxide or carbon dioxide) has been described (K. J. Jung, et al., *Informations Chemie*, 283, 135–138 (1987)), the use of this type of process for reducing the color bodies in the generation of ascorbic acid is untested. Also, a large majority of processes for decomposing furfural function in the vapor phase, and, as a consequence, are not suitable for liquid phase conversion of 2-keto-L-gulonic acid to L-ascorbic acid.

Palladium (Pd) catalysts allow for decarbonylation of furfural in the liquid phase at elevated temperatures and pressures. One example of a palladium catalyzed decarbonylation of furfural to furan utilized a barium sulfate supported palladium catalyst operating at the boiling point of furfural (162° C.) (Eschinazi, H. E., *Bull. Soc. Chim. Fr.*, 967–969 (1952)). Palladium on alumina has also been shown to be efficient in promoting decarbonylation of furfural to furan, especially when promoted by alkali metals (U.S. Pat. No. 3,007,941; E. L. Kuz'micheva, *Uzbeskskii Khimicheski Zhurnal*, 46–48 (1999)) or calcium (U.S. Pat. No. 3,257,417). Another active catalyst for decarbonylation of furfural to furan appears to be palladium on carbon (Lejemble, Ph., et al., *Chem. Lett.*, 1403–06 (1983); Lejemble, Ph. et al., *Biomass* 4, 263–74 (1984)), with the highest activity for a palladium on carbon seen in the presence of potassium carbonate. Kinetics for furfural decarbonylation using potassium carbonate assisted palladium on carbon catalyst have been described (Jung, K. J., et al., *Biomass*, 16, 63–76 (1988a)) and a commercial design proposed (Jung, K. J., et al., *Biomass*, 16, 89–96, 1988b).

Still, in designing a catalyst for the removal of the presumed color forming furfural intermediate from ascorbic acid, the prior art is neither encouraging nor predictive. Many of the processes operate in the vapor phase, which is incompatible with the aqueous conversion of 2-keto-L-gulonic acid to L-ascorbic acid. Moreover, even in the liquid phase, processes utilizing palladium on carbon are normally operated in the absence of solvent. The only studies involving a solvent used the less active palladium on alumina catalysts in the presence of a high boiling organic solvent, such as dibutyl phthalate (Japan Kokai, 1531; 1532; 1533, *Chemical Abstracts* 64, 12644 (1966).

Furthermore, furfural intermediates are believed to be the end result of consecutive conversions of 2-keto-L-gulonic acid to L-ascorbic acid, and therefore, build up over the course of the reaction. The reported turnover rates reported for undiluted furfural indicated that even the most active catalysts (e.g. palladium on carbon in the presence of potassium carbonate) (Jung, K. J., et al., 1988a) would be unable to degrade furfural intermediates at the rate they are formed during the conversion of 2-keto-L-gulonic acid to L-ascorbic acid. Dilution in water (i.e. as used for aqueous conversion 2-keto-L-gulonic acid to L-ascorbic acid) would only be expected to exacerbate the situation. In addition, all of the most effective catalysts for furfural decarbonylation have employed a basic promoter, with potassium carbonate apparently being preferred. Since 2-keto-L-gulonic acid and L-ascorbic acid are acidic, potassium carbonate is not compatible with the starting material nor the product.

The present invention describes the surprising result that palladium based catalysts reduce color bodies produced during the conversion of 2-keto-gulonic acid, or derivatives of 2-keto-gulonic acid, to ascorbic acid. Whereas the preferred substrate is 2-keto-L-gulonic acid, other derivatives of 2-keto-gulonic acid are known in the art to be suitable for the preparation of ascorbic acid, and more preferably, L-ascorbic acid. Such derivatives of 2-keto-gulonic acid include, but are not limited to, esters of 2-keto-L-gulonic acid, such as 2-keto-L-gulonic acid methyl ester, 2-keto-L-gulonic acid ethyl ester, and the like. Another preferred substrate is the bisacetonide of 2-keto-L-gulonic acid.

Normally, when palladium catalysts are used, they are placed on an inert support. When used to decolorize ascorbic acid solutions, however, the choice of support is an important component of catalyst design. Many traditional supports, such as aluminum, lead to decomposition of the reaction components 2-keto-L-gulonic acid and L-ascorbic acid. Other common supports, including silica and alkaline earth silicates, can render the catalyst ineffective for furfural decomposition. In an embodiment, the support comprises a carbon support. In another embodiment, the support comprises a barium sulfate support. Thus, the preferred catalyst would be selected from the group of catalysts consisting of palladium supported on any of a variety of carbon based supports, with palladium on barium sulfate being less preferred.

The carbon supported palladium catalysts that are preferred for this process may be generated by any of a variety of methods well known to any practitioner of the art, such as impregnation by evaporation of a solution of a palladium compound in the presence of a carbon support. Further, the desired palladium catalysts are commercially available from a variety of sources with a wide range of palladium content, a variety of particle sizes, and a wide variety of carbon sources.

The exact composition of the preferred catalyst, such as palladium content, carbon type, and particle size, are not entirely determined by chemical behavior, but in large part, are constrained by the preferred reactor configuration. Whereas several reactor configurations such as, but not limited to, stirred tank reactors (operated in continuous or batch mode), fluidized beds, and fixed bed reactors (operated as either a trickle bed or as a plug flow reactor) are usable in the process of this invention, the preferred reaction mode is to operate this reaction as a plug flow reactor. When operating the preferred plug flow reactor, larger particles are generally preferred since they have the lowest pressure drop and are least likely to become plugged during operation. However, when using less preferred alternative reactor configurations, other particle sizes might be preferred. For example, in fluidized beds or continuous stirred tank reactors, finer (smaller) particles would be preferred since finer particles facilitate dispersion throughout the reactor. Therefore, although any particle size may be used, the normal range would be between 1 μm to 5 cm more preferably, from 25 μm to 5 cm, with particle sizes of 100 μm to 2.5 cm, and 150 μm to 1.5 cm being particularly preferred.

The normal range of palladium content from commercial and laboratory sources of palladium supported on the support (ie. carbon) is 0.1–10 weight percent (wt %) palladium, where wt % palladium is grams palladium per 100 g support. Although it might be expected that catalysts containing the highest levels of palladium would be the preferred catalysts, catalysts containing high levels of palladium are normally achieved with powdered (i.e. very small particle size) supports. Generally, the preferred reactor modes for ascorbic acid synthesis require catalysts that have relatively larger particle sizes. Supporting palladium on larger sized particles sizes generally limits the achievable range of palladium content. For example, using the preferred particle sizes suitable for a plug-flow reactor range generally leads to a palladium content of from 0.1–5 wt % palladium, with 0.5–3 wt % palladium being typical. Therefore, consistent with the preferred catalyst size, the preferred range would be 0.1–10 wt % palladium, more preferably 0.1–5 wt % palladium, with the most preferred being 1–3 wt % palladium.

Any source of carbon may be used for a support in this process. Typical sources of commercial carbon supports span the range of carbon containing materials, including wood, bone, egg shell, coal, and polymers. Consistent with the preferred plug flow reactor mode of operation, the carbon supports would be selected from the carbons with particle size ranges between 1 μm to 5 cm, and more preferably, from 25 μm to 5 cm, with particle sizes of 100 μm to 2.5 cm, and 150 μm to 1.5 cm being particularly preferred. Commercial sources of carbon with these characteristics are available, and further, commercial sources of palladium supported on carbon meeting these criteria are also available. Normally, the commercial catalysts meeting these criteria are granular or are pellets generated by extruding finer carbon particles into pellets after the addition of binders and/or the application of pressure. However, when generating the catalysts, other forms may be achieved, such as spheres made when supporting the material on carbonized polymers as described in U.S. Pat. No. 6,235,673.

The catalyst may be the only catalytic material present in the reactor, or may be physically mixed with other catalytic components. Thus, in an embodiment, the reactor comprises a mixture of the palladium catalyst and a second catalyst which may be used to accelerate the conversion of 2-keto-L-gulonic acid to L-ascorbic acid while still maintaining the function of the palladium on carbon in reducing color.

The second catalyst may be a homogeneous catalyst, such as hydrochloric acid, or a heterogeneous catalyst, such as Amberlyst 15. Variations where palladium on a carbon support is used as a physical mixture with other components all fall within the scope of this invention.

Further, the presence of other elements in the catalyst is within the scope of this invention. For example, the presence of impurities in the palladium or carbon do not appear to be deleterious, although the presence of iron or manganese containing minerals may necessitate extra care to avoid the presence of oxygen and subsequent oxidation of the L-ascorbic acid product. In an another embodiment, the palladium catalyst comprises a soluble source of alkali metal or alkaline earth elements.

The source of the 2-keto-gulonic acid is unimportant in the process. Alternative processes for producing 2-keto-L-gulonic acid from glucose (S. Anderson, et al., *Science*, 230, 144–149 (1985)) or sorbose (Y. Saito, *Biotechnol. Bioeng.*, 58, 309–315, 1998) continue to be developed. Generally the starting 2-keto-L-gulonic acid is obtained by fermentation of sorbose or glucose. Preferably, an initial purification of this filtrate to remove solids using techniques such as electro dialysis, ion exchange, or crystallization is undertaken, but is not a precondition for the operation of the invention. Alternatively, the 2-keto-L-gulonic acid compound may comprise the hydrolysis products of bisacetonide of 2-keto-L-gulonic acid or the esters of 2-keto-L-gulonic acid. Regardless of the source of 2-keto-L-gulonic acid compound, it is preferred that the concentration of 2-keto-L-gulonic acid is about 1 to 40 percent, more preferably about 5 to 30 weight percent, and even more preferably, 8 to 25 weight percent.

The reactions are normally carried out in a solvent. The choice of solvent may be chosen from a wide variety of organic solvents or even water and is only limited by the solubility of the 2-keto-L-gulonic acid and its derivatives and the L-ascorbic acid product in the solvent. Since the 2-keto-L-gulonic acid and its derivatives have limited solubility in non-polar solvents, the preferred solvents would be at least moderately polar. For example, the synthesis of ascorbic acid from 2-keto-L-gulonic acid may utilize an aqueous solvent. In an embodiment, the solvent is water. In another embodiment, and especially where esters of 2-keto-L-gulonic are used, the solvent comprises the alcohol corresponding to the alkoxy moiety of the 2-keto-L-gulonic acid ester. Thus, in an embodiment the solvent is methanol. In another embodiment, the solvent is ethanol.

As defined herein, "polar" comprises molecules which have entities in which the electrons within the molecule are disproportionately distributed, resulting in a net partial negative charge and a net partial positive charge at opposing ends of the molecule. Thus, polar solvents include solvents such as water, alcohols, sulfoxide and sulfones (e.g. sulfolane), amides (dimethyl formamide, dimethyl acetamide), and nitrites. Moderately polar solvents comprise ketones, esters, and the like.

The operating pressure is dependent upon the temperature employed. Preferably, the reaction is operated over a temperature range from 25–250° C. More preferably, the reaction is operated between 75–200° C. At the highest temperatures, the vapor pressure of the water would be 25 atm (370 psi) but below 100° C. it would be less than one atm (14.6 psi). Therefore, the reaction may be operated over a very wide range of pressures, with pressures ranging from 0.1–100 atm all being practicable. However, consistent with the preferred temperature range of 75–200° C., the preferred operating pressure would be in the range of 0.7–17 atm (10–250 psi) absolute pressure.

In addition, although not critical to the operation of the present invention, it is preferred that the reaction and product be operated and stored under a non-oxidizing (oxygen depleted) atmosphere. Anaerobic storage/reaction conditions are generally accomplished by using carbon dioxide, nitrogen, argon, among other gases, often under slightly elevated pressures.

Production Systems Using Palladium Catalysts For L-Ascorbic Acid Synthesis

The present invention also provides reactors and production systems for employing palladium as a means to reduce the color of ascorbic acid. Thus, in another aspect, the present invention comprises a system for reducing the amount of color in ascorbic acid synthesized from starting material comprising 2-keto-gulonic acid or a 2-keto-gulonic acid derivative comprising a reactor for conducting the synthesis in the presence of palladium.

In an embodiment, the system comprises a reaction vessel comprising a solid palladium catalyst; at least one port in the reaction vessel to provide a means to transfer the starting material into the reaction vessel and to remove the ascorbic acid product of the synthesis from the reaction vessel; a means to heat the reaction vessel; and a means to control to the pressure in the reaction vessel.

In an embodiment, the palladium reduces the formation of colored byproducts in the reaction. Also in an embodiment, the palladium at least in part catalyses the synthesis of ascorbic acid from 2-keto-gulonic acid or 2-keto-gulonic acid derivatives. Thus, the palladium may improve the overall efficiency of the synthesis of ascorbic acid from 2-keto-gulonic acid or 2-keto-gulonic acid derivatives, as for example by removing colored intermediates that inhibit the reaction or the performance of the reactor system.

Preferably, the ascorbic acid comprises L-ascorbic acid synthesized from 2-keto-L-gulonic acid or a 2-keto-L-gulonic acid derivative. In an embodiment, the 2-keto-gulonic acid comprises an aqueous solution from a fermentation process for producing 2-keto-L-gulonic acid. In another embodiment, the 2-keto-gulonic acid comprises an aqueous solution of 2-keto-L-gulonic acid derived from the hydrolysis of the bisacetonide of 2-keto-L-gulonic acid or the esters of 2-keto-L-gulonic acid. In an embodiment, the 2-keto-gulonic acid derivative comprises a 2-keto-L-gulonic acid ester.

Preferably, the system includes a fermentation device to generate 2-keto-gulonic acid or a derivative thereof from a sugar. More preferably, the system further comprises a means to purify the 2-keto-L-gulonic acid isolated from the fermentation device for use in synthesis of ascorbic acid.

In an embodiment, the system includes a means to isolate unreacted 2-keto-gulonic acid starting material from the ascorbic acid product. Preferably, the means to isolate unreacted 2-keto-gulonic acid starting material from the ascorbic acid product comprises a device for recycling the unreacted starting material back into the reaction vessel. More preferably, the recycling means comprises a continuous separation of ascorbic acid product from unreacted 2-keto-gulonic acid starting material to form an ascorbic acid rich solution and a solution rich in 2-keto-gulonic acid compound that is recycled back into the reaction vessel.

Preferably, the synthesis of L-ascorbic acid is carried out in a solvent. More preferably, the solvent is moderately polar. In an embodiment, the solvent comprises water. Alternatively, the solvent may comprise an alcohol. Preferably, the alcohol comprises the alkoxy moiety of a 2-keto-L-gulonic acid ester used as the 2-keto-gulonic acid derivative.

In an embodiment, the reaction vessel comprises a plug flow reactor. When a plug flow reactor is used, the range of space velocities in the plug flow reactor is preferably between 0.05 $h^{-1}$ to 500 $h^{-1}$. More preferably, the range of space velocities in the plug flow reactor is between 0.1 $h^{-1}$ and 100 $h^{-1}$.

In an embodiment, the palladium is supported on a particulate substrate. Preferably, the substrate comprises carbon or barium sulfate. In an embodiment, the palladium comprises particles ranging in size from 1 μm to 5 cm. Where a plug flow reactor is used, the palladium preferably comprises particles ranging in size from 25 μm to 5 cm, more preferably, from 100 μm to 2.5 cm, and even more preferably, from 150 μm to 1.5 cm.

The reaction is generally carried out at elevated temperatures and pressures, although the pressure is dependent upon the temperature employed. Thus, at higher temperatures the vapor pressure is generally about 25 atm, but below 100° C., the pressure is less than 1 atm. Thus, the reaction vessel is preferably heated to a temperature ranging between 25° C. and 250° C. during at least a part of the synthesis, and even more preferably, the reaction vessel is heated to a temperature ranging between 75° C. and 200° C. during at least a part of the synthesis. Also preferably, the reaction vessel is maintained under an absolute pressure of from 0.1 atm to about 100 atm during at least a part of the synthesis, and even more preferably, the reaction vessel is maintained under an absolute pressure of from 0.7 atm to about 17 atm during at least a part of the synthesis.

The systems of the present invention comprise continuous as well as batch reactor formats. Although a preferred method of conducting this reaction is in a plug flow reactor, other reactor configurations are still useful and may be employed in the operation of this invention.

A plug flow reactor is particularly suited for the methods of the invention as it presents a reactor format which allows for removal of the L-ascorbic acid within a kinetic time frame such that product degradation is minimized. In an embodiment, the reactants are pushed through a reactor packed with the palladium/carbon catalyst. Alternatively, a second catalyst which enhances the conversion of 2-keto-L-gulonic acid compounds to L-ascorbic acid may be included as well. Generally, the reaction moves through the reactor as a singular mix, or "plug" such that the concentration of L-ascorbic acid at the end of the flow is increased and the concentration of 2-keto-L-gulonic acid derivative is decreased relative to the concentrations of L-ascorbic acid and 2-keto-L-gulonic acid derivative earlier in the flow.

In a plug flow reactor mode of operation, an important parameter of the reaction is the space velocity, wherein space velocity is defined as the volumetric rate of addition of the solution/volume of the reactor. Generally, the space velocity required for the reaction is a function of the desired conversion and selectivity, as well as the temperature of the reaction. Thus, although the space velocity may vary over a wide range, in a preferred embodiment, it is most likely to be determined empirically. Preferably, the range of space velocities is between 0.05 $h^{-1}$ to 500 $h^{-1}$. More preferably, the range of space velocities is between 0.1 $h^{-1}$ and 100 $h^{-1}$.

Using a plug flow reactor, the conversion of the 2-keto-L-gulonic acid compound to L-ascorbic acid is preferably taken to only partial conversion to avoid excessive degradation of L-ascorbic acid product. Also preferably, in the partial conversion mode of the present invention, separation of the solid acid catalyst from the aqueous solution of 2-keto-L-gulonic acid compound and L-ascorbic acid utilizes simple procedures known to those in the art. In an embodiment, following initial partial conversion of 2-keto-L-gulonic acid compound to L-ascorbic acid, the L-ascorbic acid is isolated, and the unreacted 2-keto-L-gulonic acid compound-is recycled back to the reactor. This separation improves overall reaction efficiency by providing for unreacted 2-keto-L-gulonic acid to be recycled back to the reactor, while minimizing decomposition of product L-ascorbic acid, thereby enhancing the overall yield of ascorbic acid. Operation of a reaction system with partial conversion of 2-keto-L-gulonic acid and a recycle step dramatically improves the overall yield to ascorbic acid. Ascorbic acid is unstable for long periods of time under the reaction conditions (e.g. P. P. Regna and B. P. Caldwell, *J. Am. Chem. Soc.*, 66, pp. 246–250, 1944), and undergoes secondary decomposition reactions. Ascorbic acid yields in a single pass process are limited by this subsequent reaction of ascorbic acid in the reactor, and the behavior follows a typical consecutive order process. Therefore, there is an optimum for single pass reactor productivity and pushing toward high conversions may be deleterious, since conditions that lead to high conversion promote decomposition of the product.

Thus, with any of the aforementioned separations, the unreacted 2-keto-L-gulonic acid compound may be recovered and recycled to the reactor. The recycled 2-keto-L-gulonic acid compound may be purified and/or concentrated prior to being recycled to the reactor. The presence of a subsequent product separation units, purification units, and recycle loops would be expected and are encompassed within the scope of this invention.

Processes for separating L-ascorbic acid from an aqueous conversion stream consisting of 2-keto-L-gulonic acid compounds and L-ascorbic acid, with efficient recycling of the 2-keto-L-gulonic acid compound, are known in the art. For example, exemplary product separation techniques for the subsequent separation and purification of L-ascorbic acid from keto-L-gulonic acid include fractional crystallization, electro-dialysis membrane separation, chromatographic methods, and the like. Generally, crystallization may be inefficient for recovering ascorbic acid directly from a process stream containing large amounts of 2-keto-L-gulonic acid, unless combined with other separation techniques (see e.g., U.S. Pat. No. 5,817,238).

Electro-dialysis membranes operated with anion exchange resins may be used to separate ascorbic acid from 2-keto-L-gulonic acid as the two components have differing pKa's (EP 0 554 090 and U.S. Pat. Nos. 4,767,870 and 6,004,455). Once separated, the 2-keto-L-gulonic acid may be recycled back to the conversion step and the ascorbic acid may be recovered.

In addition, a variety of chromatographic methods are capable of separating 2-keto-L-gulonic acid and ascorbic acid. For example, U.S. Pat. No. 5,817,238 describes a process for recovery of ascorbic acid from a filtrate solution obtained in the crystallization of ascorbic acid. Alternatively, the ascorbic acid may be adsorbed onto a resin, and then desorbed using a neutral solvent in which the concentration of the ascorbic acid in the eluent is at least as concentrated as the ascorbic acid in the aqueous feed stream (WO 97/13761). Alternatively, simulated moving bed (SMB) chromatography may be used (see e.g. commonly owned patent application Ser. Nos. 10/036,912 and 10/037,126, both filed Dec. 21, 2001, and incorporated by reference herein).

Figure 1:
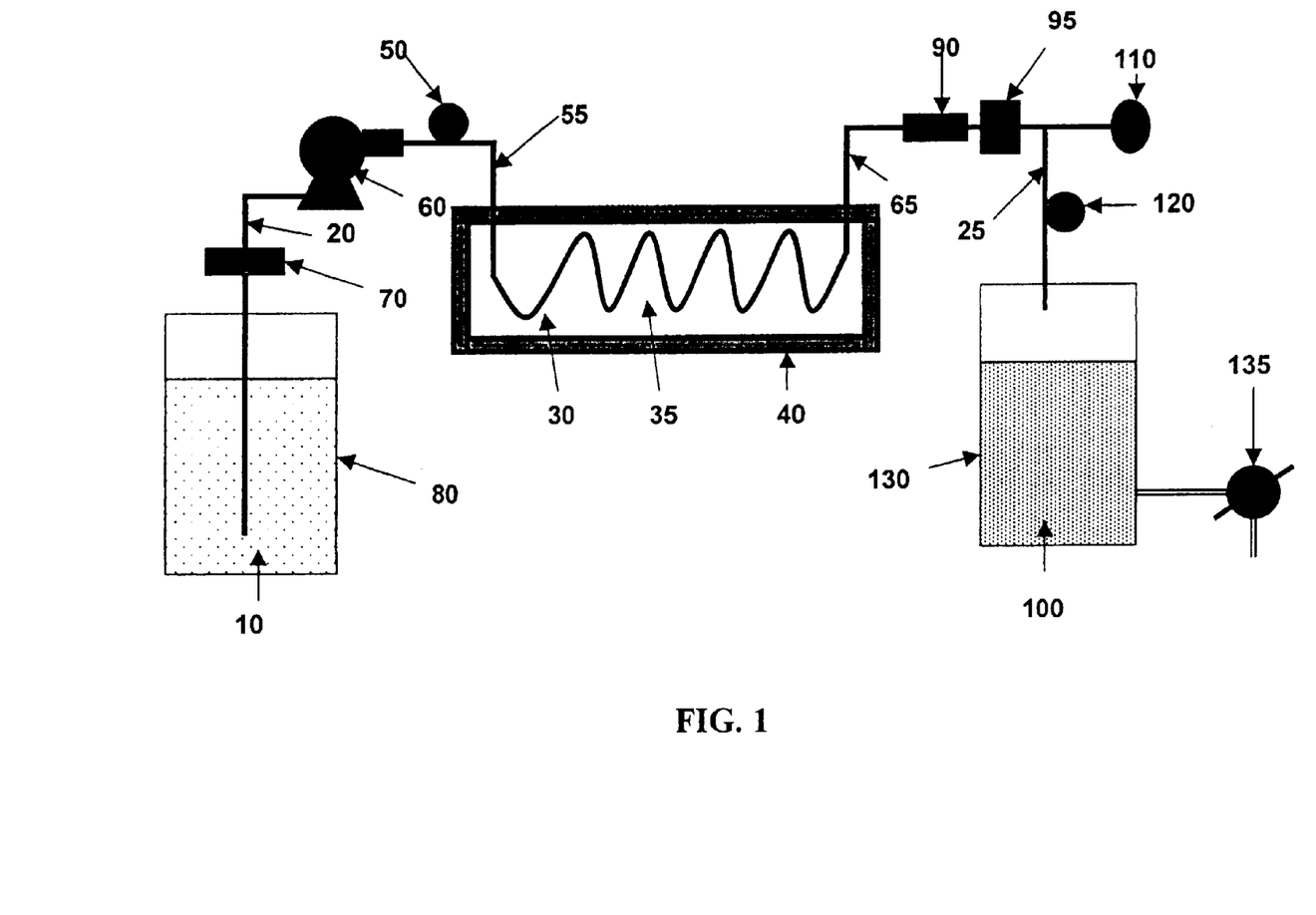
FIG. 1 illustrates a schematic of a reaction system using palladium on carbon (Pd/Carbon) for the conversion of 2-keto-L-gulonic acid to L-ascorbic acid in accordance with an embodiment of the present invention showing: 10—starting material for reaction feedstock; 20—conduit from feedstock tank into reaction vessel; 25—conduit from reaction vessel to product tank; 30—reaction vessel comprising coils containing Pd catalyst; 35—heating zone; 40—recirculating oil bath; 50—pressure gauge; 55—entry port for reaction vessel; 60—pump; 65—exit port for reaction vessel; 70—filter; 80—feedstock tank; 90—cooling coils; 95—filter; 100—ascorbic acid product; 110—pressure gauge; 120—back pressure regulator; 130—product tank; and 135—ascorbic acid product tank valve.

A schematic of a reactor system of the present invention is shown in FIG. 1. Thus, the embodiment shown in FIG. 1, feedstock comprising the 2-keto-gulonic acid substrate (10) is pumped (60) from the feedstock tank (80) via a conduit (20) into a reaction vessel (30). The pressure is controlled throughout the system using multiple pressure regulators (e.g. 50, 110) and back pressure regulators (150) as needed.

Optionally, the feedstock is filtered (70) prior to being pumped into the reaction vessel (30). The reaction vessel (30) is packed with palladium catalyst. For example, as depicted in FIG. 1, the reaction vessel (30) may comprise coils packed with solid palladium. Although the embodiment shown uses a coiled plug-flow type format, as described herein, the present invention contemplates any reactor format that allows the 2-keto-gulonic acid substrate to contact solid palladium under conditions suitable for aqueous or acidic catalysis of the 2-keto-gulonic acid substrate to ascorbic acid.

In an embodiment, the reaction vessel comprises at least one port (55) to provide transfer of the starting material into the reaction vessel. In the embodiment shown, the reaction vessel (30) also includes a second port (65) to remove the ascorbic acid product of the synthesis from the reaction vessel. Also, the system preferably comprises a means to heat the reaction vessel, such as heaters or a recirculating oil bath (40) which produces a heated zone (35), since the formation of ascorbic acid is generally under conditions of elevated temperature and reduced pressure. In an embodiment, the reaction vessel ports (55, 65) comprise leads that extend out of the heated zone.

Once the reaction is complete, or more preferably is taken to partial completion, the ascorbic acid product exits the reaction vessel (30) via at least one exit port (65) to be transferred via a conduit (25) to a product tank (130). The system may include a means for cooling (90) the reaction product, as well as filters (95) or other means to purify the product.

As described herein, the 2-keto-gulonic acid substrate may be generated by fermentation of a sugar. The fermentation system (not depicted in FIG. 1) may feed directly into the reactor, or may feed into a storage system such as the feedstock tank (80).

Also as described herein, the reaction may be taken to partial completion, with recycling of the unreacted 2-keto-gulonic acid starting material to avoid excessive degradation of L-ascorbic acid product. For example, the ascorbic acid product (100) may be treated by one of the separation techniques described herein to separate unreacted 2-keto-gulonic acid from the ascorbic acid product, with recycling of the 2-keto-gulonic acid back to the reactor (or a prereactor storage tank) and further purification of the ascorbic acid product.

EXAMPLES

The invention may be further understood by reference to the following non-limiting examples.

As described herein, two key measures of reactor performance are 2-keto-L-gulonic acid (KLG) conversion and selectivity to ascorbic acid (AsA). These are calculated simply from reactor feed and product compositions with the following expressions:

$$KLG\_Conversion\ \% = 100\% \times \left(1 - \frac{x_{KLG}^{Product}}{x_{KLG}^{Feed}}\right)$$

$$AsA\_Selectivity\ mol\% = 100\% \times \left(\frac{194.15 \times (x_{AsA}^{Product} - x_{AsA}^{Feed})}{176.13 \times (x_{KLG}^{Feed} - x_{KLG}^{Product})}\right)$$

where $x_i^j$ is the composition by weight of KLG or AsA (i) in the reactor feed or product (j).

Example 1

Preparation of Catalyst

Palladium chloride (0.532 g, 3 mmol) was dissolved in a mixture of 25 mL concentrated ammonia and 60 mL of distilled water. The solution was then added to 12×40 mesh (1.70 mm–0.425 mm) activated carbon granules (50.0 g) having a BET surface area in excess of 800 $m^2/g$ and contained in an evaporating dish. The mixture was heated on the steam bath with continuous stirring until it became free flowing and then transferred to a quartz tube measuring 106 cm long by 25 mm outer diameter. The quartz tube containing the mixture was placed in a three-element electric tube furnace so that the mixture was located in the approximate center of the 61 cm long heated zone of the furnace. Nitrogen was continuously passed through the catalyst bed at a rate of 100 standard cubic centimeters per minute, and the tube was heated from ambient temperature to 300° C. over a 2 hour period, held at 300° C. for 2 hours, and then allowed to cool back to ambient temperature. The catalyst prepared in this manner contained 1.28% Pd and had a density of 0.57 g per mL.

Example 2

Conversion of 2-Keto-L-Gulonic Acid to L-Ascorbic Acid

A solution of 2-keto-L-gulonic acid was obtained by fermentation of glucose using genetically modified Pantoea citrea followed by partial purification via microfiltration and electro dialysis. Subsequent removal of a portion of the water and crystallization provides the monohydrate of 2-keto-L-gulonic acid as a purified crystalline material. For this experiment, an aqueous solution of crystallized 2-keto-L-gulonic acid was prepared by dissolving 110 g of the crystalline 2-keto-L-gulonic acid monohydrate obtained above in 890 mL of water. The resultant solution contained 10.41 wt % 2-keto-L-gulonic acid and 0.05 wt % L-ascorbic acid by high pressure liquid chromatography (HPLC) analysis. This solution was used as feedstock throughout this experiment.

The feed system to the reactor consisted of a reservoir of aqueous 2-keto-L-gulonic acid, whose preparation and composition was described above, and was connected to a high pressure liquid chromatography (HPLC) pump using high pressure Teflon® tubing (0.318 cm ($1/8^{th}$ in) outer diameter (OD) and 0.16 cm ($1/16^{th}$ in) inner diameter (ID)). All Teflon® tubing used in this experiment was of the same dimensions unless otherwise stated, and where applicable, used PFTE fittings for connections. The outlet of the HPLC pump was connected via high pressure Teflon® tubing to a pressure relief valve set at 50 pounds per square inch (psi) followed by a pressure gauge (both constructed of 316 Stainless Steel) assembled in series using appropriate PFA reducing unions to connect the assembly to the HPLC pump.

The reactor consisted of a 74 cm (29 in) length of Teflon® PFA tubing wall thickness of 0.16 cm ($\frac{1}{16}^{th}$ in) and an outside diameter of 0.95 cm ($\frac{3}{8}^{th}$ in) (Reactor volume=21 mL). The ends of the tube were fitted with Teflon® PFA pressure fittings. The reactor was then filled by:

1) placing a small glass wool plug in the end of the reactor;
2) adding a small quantity of coarse sand (ca. 1 cm);
3) adding palladium on carbon catalyst as prepared above to within ca. 1.5 cm of the top with continuous light tapping to insure good packing; followed by
4) adding another small amount of coarse sand (ca. 1 cm.) on top of the palladium/carbon catalyst; and
5) another glass wool plug to seal the second end of the reactor.

The outlet of the feed system was attached to the inlet of the reactor using high pressure Teflon® tubing and appropriate Teflon® PFA reducing unions. The reactor should not be operated at >3.5 atm gauge pressure (51 psig) at temperatures of 150° C., since the fittings are not rated to handle reaction conditions exceeding these parameters. For safety, it is recommended that the upper temperature limit with this reactor be 140° C. and the pressure be maintained at less than 3.5 atm.

The reactor was immersed in a circulating oil bath with the outlet of the reactor attached to a 75 cm length of high pressure Teflon® tubing using appropriate PFA reducing unions. The length of high pressure Teflon® tubing was placed in a room temperature water bath and the outlet connected to a pressure gauge (316 Stainless Steel) using high pressure Teflon® PFA tubing having a wall thickness of 0.16 cm ($\frac{1}{16}^{th}$ in) and appropriate PFA reducing unions. The pressure gauge was then attached to a backpressure regulator (316 Stainless Steel), which was used to maintain the pressure in the reactor above the vapor pressure of the solvent (water). The outlet of the backpressure regulator was attached to a length of high pressure Teflon® tubing using appropriate PFA reducing unions which led into a receiving vessel (round bottom flask). A nitrogen atmosphere was maintained by placing a gas inlet with a septum on top of a round bottom flask and piercing the septum with the high pressure Teflon® tubing and attaching the gas inlet to a nitrogen source. The size of the round bottom flask required varied based on the flow rate and length of time between samples. Generally, a 50 mL or a 100 mL flask was adequate.

The temperature of the oil bath containing the reactor was raised to 145° C. and the HIPLC pump started at a flow rate of 0.50 mL/min, using the solution of 2-keto-L-gulonic acid prepared above. Samples were removed periodically and analyzed by HPLC as described below. The reactor reached steady state in about 9 hrs of operation. In this context, steady state refers to a condition of consistent chemical analysis and consistent color. At steady state, 10 samples were removed over a period of about 11 hrs.

The samples were analyzed by High Pressure Liquid Chromatography using an Inertsil ODS2 Keystone Scientific Part# 155–181, 150×4.6, 5um (DraChrom Cat# 155–181, DraChrom, Greensboro, N.C.) column and an Applied Biosystems 783a Programmable Absorbance Detector (detection wavelength: 205 nm). The mobile phase consisted of a solution of 10.55 g mono basic potassium phosphate, 3.4 g tetrabutylammonium phosphate, and 2.59 mL concentrated phosphoric acid diluted to 1000 mL in a volumetric flask with distilled water. The analytical sample was prepared by diluting 125 µL of the liquid sample from the reactor to 50 mL with water using a volumetric flask. A 5 µL sample was added to the column and eluted using a flow rate of 1.0 mL/min. Quantification was accomplished by comparison with the response for a range of standard solutions prepared by dissolving recrystallized 2-keto-L-gulonic acid and L-ascorbic acid in water at various concentrations. The standard solutions were prepared fresh and measured daily.

Figure 2:
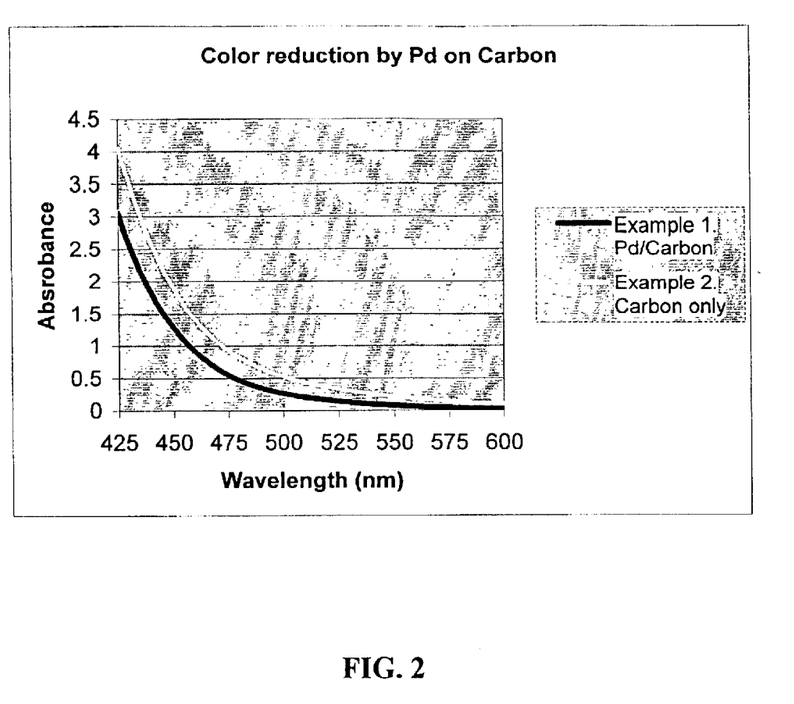
FIG. 2 illustrates a spectra for color reduction using palladium on carbon (Pd/Carbon) for the conversion of 2-keto-L-gulonic acid to L-ascorbic acid in accordance with an embodiment of the present invention.

The average concentration of the effluent from the reactor was 4.39% 2-keto-L-gulonic acid and 3.85% L-ascorbic acid. This represents a 58% conversion of 2-keto-L-gulonic acid with a selectivity to L-ascorbic acid of 71%. A visible spectrum of the effluent is shown in FIG. 2 (black line).

Example 3

Comparative Example

Example 2 was repeated except that, rather than using a palladium catalyst, the reactor was packed with the 12×40 mesh (1.70 mm–0.425 mm) activated carbon granules without any palladium added. These granules were identical (from the same container) used to generate the palladium/carbon mix.

The average concentration of the effluent from the reactor was 3.75% 2-keto-L-gulonic acid and 3.89% L-ascorbic acid. This represents a 64% conversion of 2-keto-L-gulonic acid with a selectivity to L-ascorbic acid of 65%. A visible spectrum was recorded at steady state and compared with the spectrum obtained in Example 1 (FIG. 2; white line).

Example 4

Pilot Plant Studies

This experiment was designed to test whether the system of the present invention could be scaled-up to generate production quantities of L-ascorbic acid. In addition, the experiment was designed to examine the stability of the catalyst when the system was operated for extended time periods (days and weeks).

Solutions of 2-keto-L-gulonic acid were prepared by fermentation of glucose using genetically modified *Pantoea citrea* followed by partial purification via microfiltration and electro dialysis as described for Example 2. The aqueous solutions obtained by this method contain 2-keto-L-gulonic acid and traces of L-ascorbic acid as determined by HPLC analysis. Two separate batches were obtained for this experiment and operated under two different conditions. The analysis of the feedstock is specified below for each stage of the experiment.

The reactor was constructed from a 123 inch (310 cm) length of ⅜ inch (1 cm) OD Titanium tubing with a $\frac{1}{16}^{th}$ inch (1.6 mm) wall thickness that was twisted into coils of 9 inches (23 cm) and that included leads positioned about 12 inches (30 cm) as measured from the center of the coil that connected the reaction vessel to the rest of the system. The reactor was connected at the front (input) end to a high pressure pump which pumped the feedstock through the reactor and at the back end to a collection system. The collection system included: a cooling section of jacketed tubing about one foot in length and of the same diameter, thickness, and material of construction used for the reactor; a cloth filter; a back pressure regulator; and a product collection vessel that was periodically drained and sampled.

The relative positioning of the components of the cooling system is shown in FIG. 1. The coils comprising the palladium catalyst were placed in a heated circulating oil bath.

In the first run, the oil bath was heated to 170° C. and the back pressure regulator was set at a setting of ca. 900–1000 kPa at the exit to the reactor. This setting was chosen as being sufficient to raise the pressure at the outlet of the reactor above the boiling of the aqueous reaction solvent (water) (i.e. greater than 791 kPa). The feedstock for this experiment (11.04% 2-keto-L-gulonic acid and 0.26% L-ascorbic acid) was pumped through the reactor at a rate of 14 mL/min and the reactor allowed to equilibrate for ca. 5 days before sampling began. The reactor was operated at 170° C., with a flow rate of 14 mL/min for 8 days.

Samples were collected and analyzed for ascorbic acid product and 2-keto-L-gulonic acid starting material by HPLC over the course of the experiment. Sampling was performed several times a day until the reactor reached steady state at about 5 days. At this point, sampling was performed once or twice daily. The average conversion to L-ascorbic acid was 55% with an average selectivity of 78%. Over the course of the experiment, the average color, as measured at 450 nm in a 10% dilution in water, was 0.52 absorbance units. There was little 5 variation in any of the above measurements over the course of the 8 day run.

For the second run, a visually lighter feedstock of 2-keto-L-gulonic substrate was used. Although lighter in color, this second feedstock (9.51% 2-keto-L-gulonic acid and 0.15% L-ascorbic acid), was generated by the same method as the feedstock used for the first run. For the second run, the temperature was raised to 180° C. and the pump rate was raised to 18 mL/min. To maintain the reaction solvent (water) in a liquid phase, the back pressure regulator was reset to maintain the pressure at the exit to the reactor at greater than 1001 kPa (the normal boiling point of water at this temperature). Thus, the regulator was set to maintain the pressure in the second gauge at ca. 1100–1200 kPa. The process was operated under these conditions for a total of 18 days. The average conversion to L-ascorbic acid was 59%, with an average selectivity of 70%. The average color as measured at 450 nm in a 10% dilution in water was 0.33 absorbance units. Again, there was little variation in these values throughout the operation.

Thus, this experiment demonstrated that the long-term use of the plug-flow reactor system comprising a solid palladium catalyst could be used to generate L-ascorbic acid product having reduced color levels. In addition, the continuous process produced high quality L-ascorbic acid for a total of 31 days, demonstrating stable operation for a long period of time.

With respect to the descriptions set forth above, optimum relationships of parts of the invention (to include variations in from, function, and manner of operation) are deemed readily apparent and obvious to those skilled in the art, and all equivalent relationships to those described in the specification are intended to be encompassed herein. The foregoing is considered as illustrative only of the principal of the invention. Since numerous modifications and changes will readily occur to those skilled in the art, it is not intended to limit the invention to the exact construction and operation shown and described, and all suitable modifications and equivalents falling within the scope of the appended claims are deemed within the present inventive concept.

It is to be further understood that the phraseology and terminology employed herein are for the purpose of description and are not to be regarded as limiting. Those skilled in the art will appreciate that the conception on which this disclosure is based may readily be used as a basis for designing the structures, methods and systems for carrying out the several purposes of the present invention. The claims arc regarded as including such equivalent constructions so long as they do not depart from the spirit and scope of the present invention.

What is claimed is:

1. A method for reducing the amount of color in ascorbic acid synthesized from 2-keto-gulonic acid or a 2-keto-gulonic acid derivative comprising conducting the synthesis in the presence of palladium.

2. The method of claim 1, wherein the palladium at least in part reduces the formation of colored byproducts.

3. The method of claim 1, wherein the ascorbic acid comprises L-ascorbic acid synthesized from 2-keto-L-gulonic acid or a 2-keto-L-gulonic acid derivative.

4. The method of claim 1, wherein the 2-keto-gulonic acid derivative comprises a 2-keto-gulonic acid ester.

5. The method of claim 1, wherein the 2-keto-gulonic acid comprises an aqueous solution from a fermentation process for producing 2-keto-L-gulonic acid.

6. The method of claim 1, wherein the 2-keto-gulonic acid comprises an aqueous solution of 2-keto-L-gulonic acid derived from the hydrolysis of the bisacetonide of 2-keto-L-gulonic acid or the esters of 2-keto-L-gulonic acid.

7. The method of claim 1, wherein the synthesis is carried out in a polar solvent.

8. The method of claim 1, wherein the synthesis is carried out in water.

9. The method of claim 1, wherein the synthesis is carried out in an alcohol.

10. The method of claim 9, wherein the synthesis is carried out in an alcohol corresponding to the alkoxy moiety of a 2-keto-L-gulonic acid ester used as the 2-keto-gulonic acid derivative.

11. The method of claim 1, wherein the palladium is supported on a particulate substrate.

12. The method of claim 11, wherein the substrate comprises carbon or barium sulfate.

13. The method of claim 11, wherein the palladium comprises particles ranging in size from 1 $\mu$m to 5 cm.

14. The method of claim 11, wherein the palladium comprises particles ranging in size from 25 $\mu$m to 5 cm.

15. The method of claim 11, wherein the palladium comprises particles ranging in size from 100 $\mu$m to 2.5 cm.

16. The method of claim 1, wherein the synthesis comprises heating the 2-keto-gulonic acid or 2-keto-gulonic acid derivative in the presence of palladium.

17. The method of claim 16, wherein the step of heating is at a temperature of from about 25° C. to about 250° C.

18. The method of claim 16, wherein the step of heating is at a temperature of from about 75° C. to about 200° C.

19. The method of claim 16, wherein the step of heating is under an absolute pressure of from 0.1 atm to about 100 atm.

20. The method of claim 16, wherein the step of heating is under an absolute pressure of from 0.7 atm to about 17 atm.

21. The method of claim 1, wherein the synthesis of ascorbic acid from 2-keto-L-gulonic acid comprises an aqueous solution of 1 to 40 weight percent 2-keto-L-gulonic acid or 2-keto-gulonic acid derivative.

22. The method of claim 1, wherein the synthesis comprises an aqueous solution of 5 to 30 weight percent 2-keto-L-gulonic acid or 2-keto-gulonic acid derivative.

23. The method of claim 1, wherein the synthesis comprises an aqueous solution of 8 to 25 weight percent 2-keto-L-gulonic acid or 2-keto-gulonic acid derivative.

24. The method of claim 1, wherein the conversion of 2-keto-gulonic acid or a derivative thereof to ascorbic acid is taken to only partial conversion.

25. The method of claim 24, further comprising the steps of:
removing from the synthesis a post-reaction solution comprising unreacted 2-keto-gulonic acid or a derivative thereof and ascorbic acid product;
separating the ascorbic acid from the unreacted 2-keto-gulonic acid compound in the post-reaction solution to form an ascorbic acid rich solution and a solution rich in unreacted 2-keto-gulonic acid compound; and
recycling the solution comprising unreacted 2-keto-gulonic acid compound back to the reactor.

26. The method of claim 1, wherein the palladium is mixed with a second catalyst for increasing the conversion of starting 2-keto-gulonic acid or 2-keto-gulonic acid derivative to ascorbic acid.

27. The method of claim 1, wherein the synthesis is carried out in a plug flow reactor.

28. Ascorbic acid synthesized from 2-keto-gulonic acid or a 2-keto-gulonic acid derivative in the presence of palladium.

29. The ascorbic acid of claim 28, wherein the ascorbic acid comprises reduced color compared to ascorbic acid synthesized from 2-keto-gulonic acid or a 2-keto-gulonic acid derivative in the absence of palladium.

30. The ascorbic acid of claim 28, wherein the palladium at least in part reduces the formation of colored byproducts.

31. The ascorbic acid of claim 28, further comprising L-ascorbic acid synthesized from 2-keto-L-gulonic acid or a 2-keto-L-gulonic acid derivative.

32. The ascorbic acid of claim 28, wherein the 2-keto-gulonic acid comprises an aqueous solution from a fermentation process for producing 2-keto-L-gulonic acid.

33. The ascorbic acid of claim 28, wherein the 2-keto-gulonic acid comprises an aqueous solution of 2-keto-L-gulonic acid derived from the hydrolysis of the bisacetonide of 2-keto-L-gulonic acid or the esters of 2-keto-L-gulonic acid.

34. The ascorbic acid of claim 28, wherein the 2-keto-gulonic acid derivative comprises a 2-keto-L-gulonic acid ester.

35. The ascorbic acid of claim 28, wherein the synthesis is carried out in a polar solvent.

36. The ascorbic acid of claim 28, wherein the synthesis is carried out in water.

37. The ascorbic acid of claim 28, wherein the synthesis is carried out in an alcohol.

38. The ascorbic acid of claim 37, wherein the synthesis is carried out in an alcohol corresponding to the alkoxy moiety of a 2-keto-L-gulonic acid ester used as the 2-keto-gulonic acid derivative.

39. The ascorbic acid of claim 28, wherein the palladium is supported on a particulate substrate.

40. The ascorbic acid of claim 39, wherein the substrate comprises barium sulfate or carbon.

41. The ascorbic acid of claim 39, wherein the palladium comprises particles ranging in size from 1 $\mu$m to 5 cm.

42. The ascorbic acid of claim 39, wherein the palladium comprises particles ranging in size from 25 $\mu$m to 5 cm.

43. The ascorbic acid of claim 39, wherein the palladium comprises particles ranging in size from 100 $\mu$m to 2.5 cm.

44. The ascorbic acid of claim 28, wherein the conversion of 2-keto-gulonic acid or a derivative thereof to ascorbic acid is taken to only partial conversion.

45. The ascorbic acid of claim 44, wherein the ascorbic acid product is separated from unreacted 2-keto-gulonic acid or a derivative thereof.

46. The ascorbic acid of claim 28, wherein the synthesis is carried out in a plug flow reactor.

47. A system for reducing the amount of color in ascorbic acid synthesized from 2-keto-gulonic acid or a 2-keto-gulonic acid derivative as starting material comprising a reactor for conducting the synthesis in the presence of palladium.

48. The system of claim 47, further comprising:
a reaction vessel comprising solid palladium;
at least one port in the reaction vessel to provide a means to transfer the starting material into the reaction vessel and to remove the ascorbic acid product of the synthesis from the reaction vessel;
a means to heat the reaction vessel; and
a means to control to the pressure in the reaction vessel.

49. The system of claim 47, wherein the palladium at least in part reduces the formation of colored byproducts in the reaction.

50. The system of claim 47, wherein the ascorbic acid comprises L-ascorbic acid synthesized from 2-keto-L-gulonic acid or a 2-keto-L-gulonic acid derivative.

51. The system of claim 47, wherein the 2-keto-gulonic acid derivative comprises a 2-keto-L-gulonic acid ester.

52. The system of claim 47, wherein the 2-keto-gulonic acid comprises an aqueous solution from a fermentation process for producing 2-keto-L-gulonic acid.

53. The system of claim 47, wherein the 2-keto-gulonic acid comprises an aqueous solution of 2-keto-L-gulonic acid derived from the hydrolysis of the bisacetonide of 2-keto-L-gulonic acid or the esters of 2-keto-L-gulonic acid.

54. The system of claim 47, further comprising a fermentation device to generate 2-keto-L-gulonic acid or a derivative thereof from a sugar.

55. The system of claim 54, further comprising a means to purify the 2-keto-L-gulonic acid isolated from the fermentation device for use in synthesis of ascorbic acid.

56. The system of claim 47, further comprising a means to isolate unreacted 2-keto-gulonic acid starting material from the ascorbic acid product.

57. The system of claim 56, wherein the means to isolate unreacted 2-keto-gulonic acid starting material from the ascorbic acid product comprises a device for recycling at least a part of the unreacted 2-keto-gulonic acid starting material back into the reaction vessel.

58. The system of claim 57, wherein the recycling means comprises a continuous separation of ascorbic acid product from unreacted 2-keto-gulonic acid starting material to form an ascorbic acid rich solution and a solution rich in 2-keto-gulonic acid compound that is recycled back into the reaction vessel.

59. The system of claim 47, wherein the synthesis is carried out in a polar solvent.

60. The system of claim 47, wherein the synthesis is carried out in water.

61. The system of claim 47, wherein the synthesis is carried out in an alcohol.

62. The system of claim 61, wherein the synthesis is carried out in an alcohol corresponding to the alkoxy moiety of a 2-keto-L-gulonic acid ester used as the 2-keto-gulonic acid derivative.

63. The system of claim 48, wherein the reaction vessel comprises a plug flow reactor.

64. The system of claim 63, wherein the range of space velocities in the plug flow reactor is between 0.05 $h^{-1}$ to 500 $h^{-1}$.

65. The system of claim 63, wherein the range of space velocities in the plug flow reactor is between 0.1 $h^{-1}$ and 100 $h^{-1}$.

66. The system of claim 47, wherein the palladium is supported on a particulate substrate.

67. The system of claim 66, wherein the substrate comprises carbon or barium sulfate.

68. The system of claim 66, wherein the palladium comprises particles ranging in size from 25 μm to 5 cm.

69. The system of claim 66, wherein the palladium comprises particles ranging in size from 100 μm to 2.5 cm.

70. The system of claim 48, wherein the reaction vessel is heated to a temperature ranging between 25° C. and 250° C. during at least a part of the synthesis.

71. The system of claim 48, wherein the reaction vessel is heated to a temperature ranging between 75° C. and 200° C. during at least a part of the synthesis.

72. The system of claim 48, wherein the reaction vessel is maintained under an absolute pressure of from 0.1 atm to about 100 atm during at least a part of the synthesis.

73. The system of claim 48, wherein the reaction vessel is maintained under an absolute pressure of from 0.7 atm to about 17 atm during at least a part of the synthesis.

* * * * *

UNITED STATES PATENT AND TRADEMARK OFFICE
CERTIFICATE OF CORRECTION

PATENT NO. : 6,716,997 B1
DATED : April 6, 2004
INVENTOR(S) : Joseph R. Zoeller

It is certified that error appears in the above-identified patent and that said Letters Patent is hereby corrected as shown below:

Column 9,
Line 63, the word "nitrites" should read -- nitriles --

Column 11,
Line 29, delete the period after the Celsius symbol for "100° C." to read -- 100° C --
Line 31, delete the period after the Celsius symbol for "25° C." to read -- 25° C --
Line 32, delete the period after the Celsius symbol for "250° C." to read -- 250° C --
Line 34, delete the period after the Celsius symbol for "75° C." to read -- 75° C --
Line 34, delete the period after the Celsius symbol for "200° C." to read -- 200° C --

Column 14,
Lines 33 and 34, delete the period after the Celsius symbol for "300° C." to read
-- 300° C --

Column 15,
Line 53, delete the period after the Celsius symbol for "145° C." to read -- 145° C --

Column 17,
Line 24, that portion reading "little 5 variation" should read -- little variation --

Column 18,
Line 49, delete the period after the Celsius symbol for "25° C." to read -- 25° C --
Line 51, delete the period after the Celsius symbol for "75° C." to read -- 75° C --

Column 20,
Line 63, that portion reading "0.05 h $^{31\ 1}$" should read -- 0.05 h$^{-1}$ --

Column 21,
Line 10, delete the period after the Celsius symbol for "25° C." to read -- 25° C --
Line 10, delete the period after the Celsius symbol for "250° C." to read -- 250° C --

UNITED STATES PATENT AND TRADEMARK OFFICE
CERTIFICATE OF CORRECTION

PATENT NO.    : 6,716,997 B1
DATED         : April 6, 2004
INVENTOR(S)   : Joseph R. Zoeller It is certified that error appears in the above-identified patent and that said Letters Patent is hereby corrected as shown below:

Column 22,
Line 2, delete the period after the Celsius symbol for "75° C." to read -- 75° C --
Line 2, delete the period after the Celsius symbol for "200° C." to read -- 200° C --

Signed and Sealed this

Sixteenth Day of November, 2004

JON W. DUDAS
*Director of the United States Patent and Trademark Office*